(12) United States Patent
Navas et al.

(10) Patent No.: US 8,690,890 B2
(45) Date of Patent: Apr. 8, 2014

(54) ORBIT DISTRACTOR

(76) Inventors: Maria Del Carmen Navas, San Jose' (CR); Sergio Hernandez, San Jose (CR)

( * ) Notice: Subject to any disclaimer, the term of this patent is extended or adjusted under 35 U.S.C. 154(b) by 631 days.

(21) Appl. No.: 12/863,768

(22) PCT Filed: Feb. 6, 2008

(86) PCT No.: PCT/CR2008/000001
§ 371 (c)(1),
(2), (4) Date: Aug. 26, 2010

(87) PCT Pub. No.: WO2009/097827
PCT Pub. Date: Aug. 13, 2009

(65) Prior Publication Data
US 2011/0009913 A1 Jan. 13, 2011

(51) Int. Cl.
*A61B 17/62* (2006.01)
*A61B 17/66* (2006.01)
*A61B 17/56* (2006.01)

(52) U.S. Cl.
USPC ............... 606/105; 606/57; 606/90; 602/17

(58) Field of Classification Search
USPC ....... 606/53–59, 86 R, 90, 105, 71, 281, 282, 606/902, 903; 623/6.64; 600/210, 214–219, 600/224, 225, 231, 232, 235, 236; 602/17; 81/397, 485
See application file for complete search history.

(56) References Cited

U.S. PATENT DOCUMENTS 4,997,445 A * 3/1991 Hodorek .................... 623/23.51
2005/0251136 A1* 11/2005 Noon et al. .................... 606/56

* cited by examiner

*Primary Examiner* — Michael T Schaper
(74) *Attorney, Agent, or Firm* — Fish & Richardson P.C.

(57) ABSTRACT

In one aspect, an apparatus for correcting osseous development deficiencies at orbital level in persons includes a halo-like structure for fixing to a cranium, a union plate between the halo-like structure and the distractor, and the orbital distractor itself, which is supported by the halo-like structure and fixed to the orbit.

19 Claims, 5 Drawing Sheets

1.a. Titanium ring
1.b. Holes for supporting the union plate
1.c. Circular bars 5.a. Outer threaded cylinder
5.b. Cylinders
5.c. Bracket plate
5.d. Connectors
5.e. Handle 1.a. Titanium ring
1.b. Holes for supporting the union plate
1.c. Circular bars 2.a. Holes for securing the stabilizing bars to the union plate.

3.a. Movable bridge-shaped plate
3.b. Adjustment and fastening screw system
3.c. Threaded holes 4.a. Union plate
4.b. Perforation in flat side
4.c. Total opening perforation
4.d. Threaded hole for inserting the distractor 5.a. Outer threaded cylinder
5.b. Cylinders
5.c. Bracket plate
5.d. Connectors
5.e. Handle

ORBIT DISTRACTOR

CROSS-REFERENCE TO RELATED APPLICATIONS

This application is the National Stage of International Application No. PCT/CR2008/000001, filed on Feb. 6, 2008, the contents of which are hereby incorporated by reference in their entirety.

TECHNICAL FIELD

This disclosure relates to correction processes of osseous development anomalies, more specifically, with regards to malformations that develop or bring about a deficiency in the ocular orbit development.

BACKGROUND

Today a significant number of patients with congenital or acquired defects in the ocular globe are treated successfully with ocular prostheses adaptation, achieving the stimulation necessary for the proper development of the orbit bone component. Opposing to this, there is a group of patients where this adaptation cannot be made due to the lack of space resulting from development deficiency, and, up to date, there is no other alternative effective treatment method.

SUMMARY

The present disclosure is focused on an apparatus that, after being implanted surgically, enables the stimulation of the orbit's progressive development in posteroanterior, superoinferior and lateral direction.

DETAILED DESCRIPTION

Figure 1:
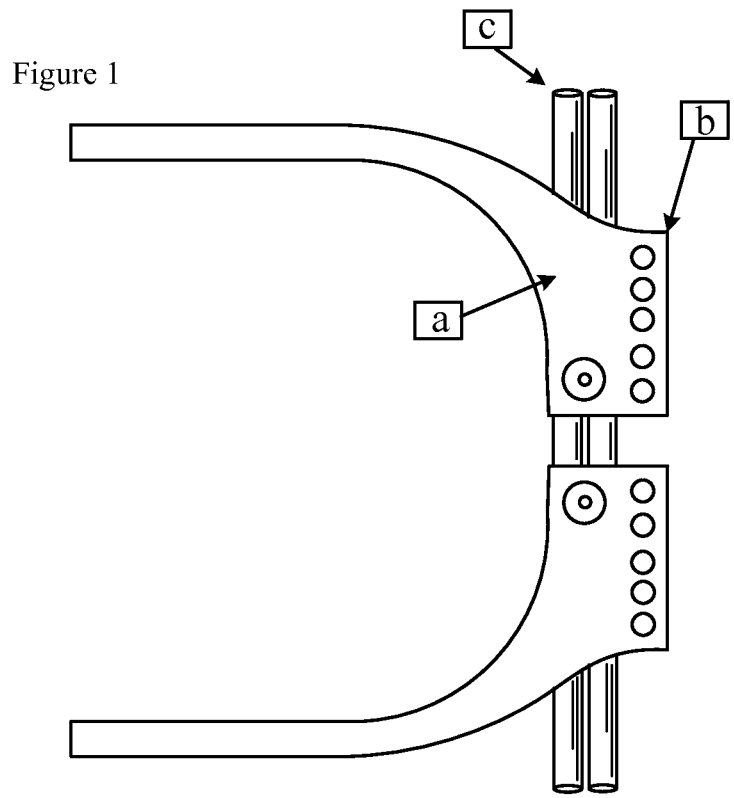
FIG. 1 shows a halo-like structure for fixing to the cranium.
Figure 2:
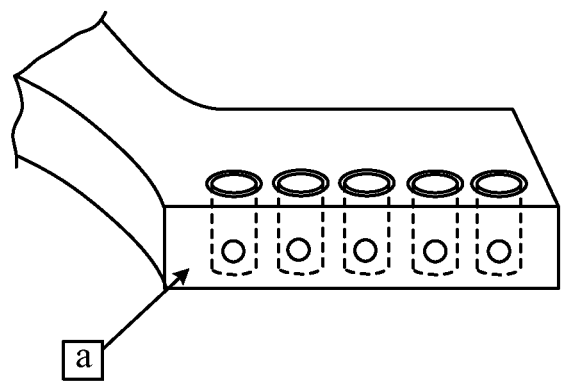
FIG. 2 shows a portion of the halo-like structure of FIG. 1.
Figure 3:
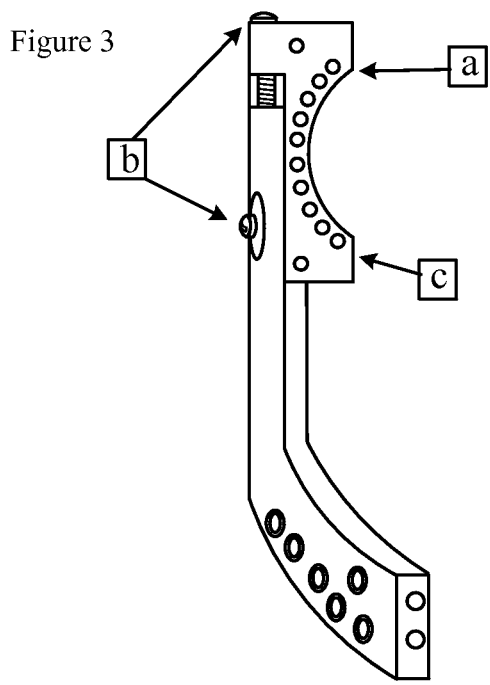
FIG. 3 shows a bridge-shaped plate.
Figure 4:
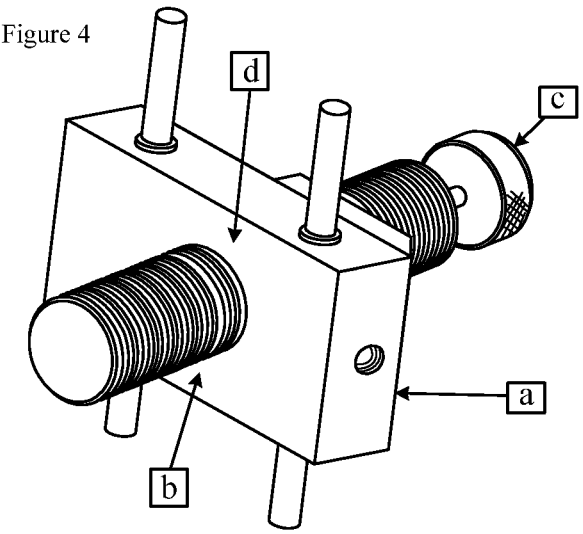
FIG. 4 shows a union plate.
Figure 5:
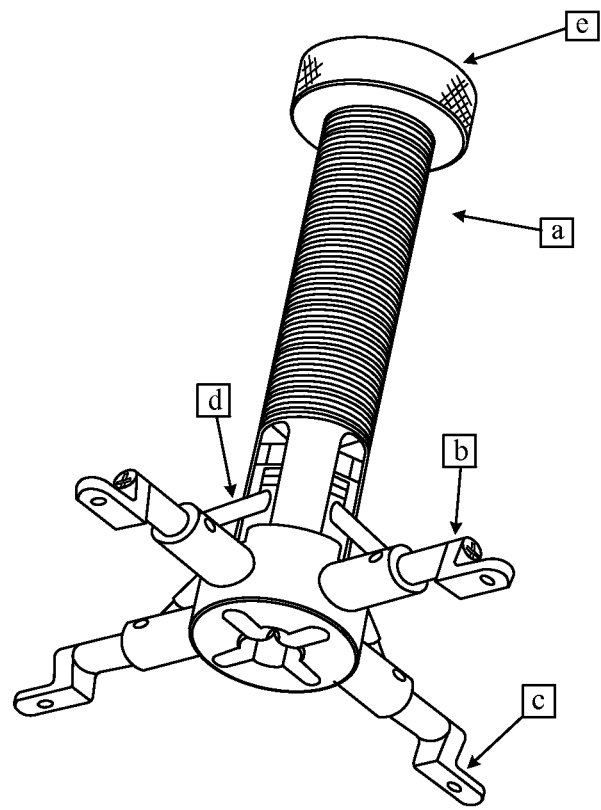
FIG. 5 shows an orbital distractor.

This disclosure relates to a novel apparatus for persons presenting with a significant degree of deficiency in terms of orbit bone development. This novel apparatus is produced from titanium and comprises three devices, i.e. a halo-like structure for fixing to the cranium, a plate for connecting between the devices, and a device carried by the halo-like structure mentioned previously. The novel apparatus is secured to the orbit in order to bring about expansion. Said device is known as a distractor.

In some implementations, the apparatus is comprised of the following components in its manufacturing process. One component is a three-quarters circle titanium ring 1.a that is fixed to the cranium and serves as a supporting means for the orbit distractor. The latter is formed by two semicircles, one of them being the mirror image of the other. The front section of the semicircle is flat and rectangular. In the frontmost section of said flat area there are five holes in superoinferior direction 1.b—equidistant from each other—which enable the passing of the fixing bars 4.c of the stabilizing plate. Further, the halo-like structure in the front face has five threaded equidistant holes 2.a from front to back, matching with the five superoinferior holes. In the posterior half of the flat section there are two holes in the lateral side along its entire length, where two titanium circular bars (horizontally) 1.c can be inserted, separated from each other, in order to enable the lateral movement of said two semicircles. Each semicircle can be maintained in its final specific position by means of a fastening screw mounted on a washer that secures those bars, preventing the ring from moving.

The posterior section of the halo-like structure—in its inferior side—has a bridge-shaped plate 3.a, with upward convexity, which can be moved backwards by a screw 3.b activated in its posterior section for fitting in the cranium. The bridge-shaped plate has a channel or rail in its superior section that enables its better displacement. A screw in the superior section 3.b is used to fix the plate in the final specific section. Mounted on a washer, the screw can pass through the oval hole of the titanium ring in its superoposterior section, which, then, is introduced directly in a screw hole of the same size within the plate. In that way, the bridge-shaped plate is fixed and cannot move from the desired position. This bridge-shaped plate is detachable and will have 12 circular threaded holes 3.c for inserting the screws that can be mounted on the cranium as a supporting means for the whole apparatus. The holes and screws are of the same size. The screw is an Allen screw.

The union plate 4.a is a device that joins the halo-like structure or titanium ring with the distractor. This union plate is provided with two parallel holes 4.c equidistant from the edges and that go through the plate completely. Perpendicular to these holes, there is a threaded hole 4.b that penetrates in up to the tunnel formed by the hole in its journey. This hole has an Allen screw for fixing the union bars between the plate and the fastening halo-like structure. In its widest side it has a threaded ring 4.d, which enables the insertion of the threaded section of the outer cylinder of the distractor. This distractor is comprised of a stem with a proximal outer threading 5.a presenting four equidistant grooves in the opposing end of the threading section. Distally to these grooves, the stem has four holes where 4 cylinders 5.b are placed to enable the displacement of the wheel axles; in that way, they can be opened and closed until they can converge with each other—movement that can be achieved by means of 4 connectors 5.d sliding through the grooves with longitudinal movements. These connectors are connected to the wheel axles allowing them to move transversally through the little cylinders, which have a small groove, partially longitudinal, that allows the 4 booms to displace and, thus, achieving a continuous adjustment movement of the wheels. This movement can be regulated by means of a threaded axle, which slides interiorly across the main cylinder by means of a gear system that limits the movement of the wheels at 0.25 mm per round applied to the internal stem. The latter has a handle 5.e with a graphic corresponding to the wheels' opening in millimeters.

The wheels are four bracket plates 5.c with distal and horizontal perforation. The proximal and vertical section is perforated to be joined by using a screw to the wheel axles.

The system movement from back to front can be achieved by gearing the threaded section of the main axle with the inner thread of the plate hole we have described above.

The invention claimed is:
1. An apparatus for correcting osseous development deficiencies at orbital level in persons, the apparatus comprising:
a halo-like structure for fixing to a cranium,
a union plate attached to the halo-like structure, and
an orbital distractor, supported by the union plate from the halo-like structure and fixable to an orbit, the orbit distractor comprising:

a stem including a main outer cylinder containing an inner threaded axle, the outer cylinder defining four grooves;

four secondary cylinders mounted on the stem;

four connecting booms, each connecting boom extending through one of the grooves and linking one of the secondary cylinders to the threaded axle such that movement of the threaded axle within the main outer cylinder controls movement of the four secondary cylinders.

2. The apparatus according to claim 1, wherein the halo-like structure for fixing to the cranium comprises a three-quarters circle titanium ring.

3. The apparatus according to claim 1 wherein the halo-like structure for fixing to the cranium comprises two semicircles, one being a mirror image of the other.

4. The apparatus according to claim 1 wherein the halo-like structure for fixing to the cranium comprises a titanium ring having perforations in its superior and front section for supporting the union plate.

5. The apparatus according to claim 1 wherein the halo-like structure for fixing to the cranium comprises a titanium ring having perforations in its frontal section, from front to back, for adjusting stabilizing bars of the union plate.

6. The apparatus according to claim 1 wherein the halo-like structure for fixing to the cranium comprises a titanium ring having two horizontal circular bars that enable the displacement and adjustment of the titanium ring to a size of the cranium.

7. The apparatus according to claim 1 wherein the halo-like structure for fixing to the cranium comprises a titanium ring having, in its posterior section, a movable bridge-shaped plate, with upward convexity, for adjusting the ring in the posterior section of the cranium.

8. The apparatus according to claim 1 wherein the halo-like structure for fixing to the cranium comprises a titanium ring having, in its posterior section, a movable plate that is adjustable by a screw system in its end section.

9. The apparatus according to claim 1 wherein the halo-like structure for fixing to the cranium comprises a titanium ring having, in its posterior section, a movable bridge-shaped plate containing holes in its lateral side for inserting screws that will secure the halo-like structure to the cranium.

10. The apparatus according to claim 1 wherein the union plate is provided with two holes in its flat sides for inserting supporting bars through the halo-like fixing structure.

11. The apparatus according to claim 1 wherein the union plate has, in its widest side, a complete opening, threaded and tunnel-shaped perforation for supporting the orbital distractor.

12. The apparatus according to claim 11 wherein posteroanterior movement of the apparatus is achieved by gearing an outer threaded section of the main outer cylinder with an internal thread of the perforation of the union plate.

13. The apparatus according to claim 1 wherein the main outer cylinder enables posterior-anterior movement.

14. The apparatus according to claim 1 wherein the orbit distractor comprises four bracket plates, each bracket plate attached to a free end of one of the four secondary cylinders.

15. The apparatus according to claim 1 wherein the four connecting booms are attached to wheel axles that control transverse movement of the four secondary cylinders.

16. The apparatus according to claim 1 wherein opening and closing movement graduation of the orbit distractor is controlled by means of a gear system that limits movement of wheels.

17. The apparatus according to claim 1 wherein the inner threaded axle comprises a handle that includes a graphic of opening and closing movement in millimeters.

18. The apparatus according to claim 1 wherein graduation of the orbit distractor for each movement corresponds to 0.25 mm per round of the inner threaded axle.

19. The apparatus according to claim 1 wherein the orbit distractor comprises a gear system between the main outer cylinder and the union plate.

* * * * *